(12) United States Patent
Heaney et al.

(10) Patent No.: US 6,479,537 B2
(45) Date of Patent: Nov. 12, 2002

(54) SYNERGISTIC ECTOPARASITICIDAL METHODS AND COMPOSITIONS

(75) Inventors: Kathleen Heaney, Yardley, PA (US); Mary E. Doscher, Trenton, NJ (US); Douglas Rugg, Lebanon, NJ (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/990,600

(22) Filed: Nov. 21, 2001

(65) Prior Publication Data

US 2002/0091149 A1 Jul. 11, 2002

Related U.S. Application Data

(60) Provisional application No. 60/252,710, filed on Nov. 22, 2000.

(51) Int. Cl.[7] .......................... A01N 43/36; A01N 43/02
(52) U.S. Cl. ........................................ 514/427; 514/450
(58) Field of Search .................................. 514/427, 450

(56) References Cited

U.S. PATENT DOCUMENTS 4,916,154 A    4/1990   Asato et al. ................ 514/450
5,455,263 A   10/1995   Doscher et al. ............. 514/422

FOREIGN PATENT DOCUMENTS

EP         0 714 894 A1    6/1996
WO         WO 98/23154     6/1998

OTHER PUBLICATIONS

Malleron et al., New Indole Derivatives as Potent and Selective Serotonin Uptake Inhibitors, J. Med. Chem 1993, 36, 1194–1202.

*Primary Examiner*—Allen J. Robinson
(74) *Attorney, Agent, or Firm*—Joseph M. Mazzarese

(57) ABSTRACT

The present invention provides methods for synergistic control of ectoparasitic arthropods with a synergistically effective amount of a combination of the macrocyclic lactone moxidectin and an arylpyrrole compound. Also provided are methods of protecting animals from infestation and attack by ectoparasites with said combination. The present invention also provides synergistic insecticidal compositions comprising as essential active ingredients the macrocyclic lactone moxidectin and an arylpyrrole compound.

19 Claims, No Drawings

SYNERGISTIC ECTOPARASITICIDAL METHODS AND COMPOSITIONS

This application claims priority from copending provisional application Ser. No. 60/252,710, filed on Nov. 22, 2000, the entire disclosure of which is hereby incorporated by reference.

BACKGROUND OF THE INVENTION

Although insecticidal agents have been developed to control insect and acarid pests such as agrohorticultural pests, animal ectoparasites or hygienic pests, and in practice have been used as a single or a mixed agent, economically efficient and ecologically safe control agents are still being sought. Insecticides or acaricides which allow for reduced effective dosage rates, increased environmental safety and lower the incidence of resistance are highly desirable.

Examples of such agents are found in U.S. Pat. No. 4,916,154, which discloses the anthelmintic, insecticidal, ectoparasiticidal, nematicidal and acaricidal activity of macrocyclic lactones, and in U.S. Pat. No. 5,455,263, which teaches that a broad spectrum of arylpyrrole compounds is known to be useful for the control of endo- and ectoparasites on warm-blooded mammals.

The rotational application of control agents having different modes of action may be adopted for good pest management practice, but this approach does not necessarily give satisfactory control. Combinations of control agents have been studied, but these do not always exhibit high synergistic action. Obtaining a composition which demonstrates no cross-resistance to existing agents, no toxicity problems and little negative impact on the environment is extremely difficult.

Therefore it is an object of this invention to provide novel methods for synergistic ectoparasite control and protecting animals from infestation and attack by insects, ticks and mites.

It is another object of this invention to provide novel synergistic ectoparasiticidal compositions.

Other objects and advantages of the present invention will be apparent from the disclosure below and the attached claims.

SUMMARY OF THE INVENTION

The present invention provides a method for the control of insects, mite and ticks which comprises contacting said insects or their host, habitat, breeding area, or food supply with a synergistically effective amount of a combination of the macrocyclic lactone moxidectin having the formula I

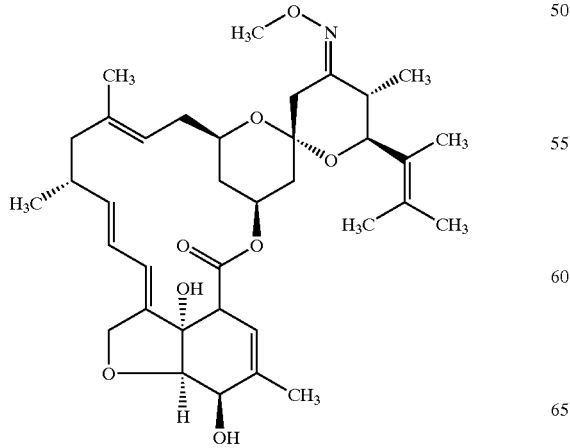

and an arylpyrrole compound of formula II

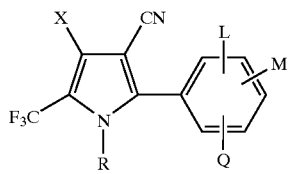

wherein R is hydrogen or $C_1$–$C_4$alkoxymethyl;

X is Cl or Br, and

L, M, and Q are each independently hydrogen, Cl, Br, I, F or $C_1$–$C_4$ haloalkyl.

Also provided are methods of protecting animals from infestation and attack by insects, ticks and mites which comprises administering to the animals a synergistically effective amount of said combination.

The present invention further provides a synergistic ectoparasiticidal composition which comprises a synergistically effective amount of a combination of moxidectin and said arylpyrrole.

DETAILED DESCRIPTION OF THE INVENTION

When two or more substances in combination demonstrate unexpectedly high biological activity, for example, insecticidal activity, the resulting phenomenon may be referred to as synergism. The mechanism of synergism is not fully understood, and quite possibly may differ with different combinations. However, the term "synergism" as used in this application designates a cooperative action encountered in a combination of two or more biologically active components in which the combined activity of the two or more components exceeds the sum of the activity of each component alone.

Surprisingly, it has now been found that combinations of the macrocyclic lactone moxidectin having formula I

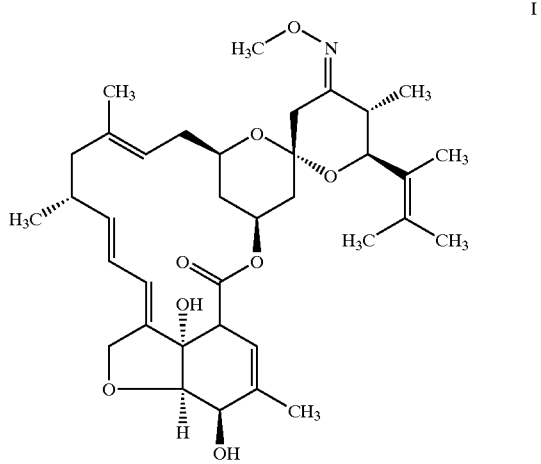

and an arylpyrrole of formula II

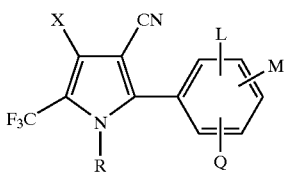

wherein R, X, L, M, and Q are defined as above, provide superior control at lower levels of the combined active agents than may be achieved when moxidectin or the arylpyrrole is applied alone. Preferred arylpyrrole compounds are those of formula II
wherein
X is Br;
R is hydrogen or ethoxymethyl;
L and Q are hydrogen; and
M is 4-Cl or 4-Br.

Among the formula II arylpyrrole compounds particularly useful in the method of the invention is 4-bromo-2-(p-chlorophenyl)-1-(ethoxymethyl)-5-(trifluoromethyl) pyrrole-3-carbonitrile, commonly known as chlorfenapyr.

The present invention also provides methods for the protection of animals from infestation and attack by insects and acarids. Important agronomic and companion animals such as cattle, sheep, horses, pigs, goats, water buffalo, llamas, deer, cats, dogs, rabbits, and the like, are prone to attack and infestation by biting and sucking insects, such as Diptera, Phthiraptera and Siphonaptera, and parasitic Acarina such as mites and ticks. In particular, Diptera: Muscidae such as *Musca autumnalis* (face flies), *Haematobia irritans* (horn flies), *Stomoxys calcitrans* (stable flies), heel flies, tsetse flies, and the like, are breeders of filth and vectors of disease and are serious pests of animals such as cattle, horses and sheep. Further, Diptera: Hippoboscidae (louse flies) such as *Melophagus ovinus* (sheep ked), which is a serious parasite of sheep, are problematic in animal production.

Among the Phthiraptera families known to be parasites of animals are: Trichodectidae such as *Bovicola bovis* (important cattle-biting louse) or *B. equi* (horse-biting louse); Haematopinidae such as *Haematopinus suis* (hog louse), or *H. asini* (horse sucking louse); Linognathidae such as *Linognathus stenopsis* (goat sucking louse) or *L. vitali* (long-nosed cattle louse); and the like.

One of the Siphonaptera families known to infest companion animals is Pulicinae such as Archaeopsyllinae (cat and dog fleas), Spilopsyllinae (rabbit fleas), and the like.

From the order of the Acarina, for example, Argas spp., Omithodoros spp., *Dermanyssus gallinae*, Boophilus spp., Rhipicephalus spp., Amblyomma spp., Dermacentor spp., Hyalomma spp., Ixodes spp., Psoroptes spp., Choriopes spp., Sarcoptes spp., are some of the ticks and mites known to infest domesticated animals and birds.

The methods and compositions of this invention may be used for combating and preventing infestation of many of the aforementioned pests.

The effective amount of the synergistically effective combination of the macrocyclic lactone moxidectin (formula I) and an arylpyrrole of formula II to be used in the method of this invention will vary according to the specific arylpyrrole compound used, the mode of application, the insect pest to be controlled, the degree of infestation, the extent of the insect population, the nature of the target host, the weather conditions, and the like. Effective dosages may range from about 0.001 mg/kg to 10.0 mg/kg, preferably about 0.01 mg/kg to 10.0 mg/kg.

The present invention also provides a synergistic ectoparasiticidal composition comprising an acceptable carrier and a synergistically effective amount of a combination of the macrocyclic lactone moxidectin and an arylpyrrole of formula II. It has been found that the active ingredients of the invention are highly synergistic when present at a ratio of moxidectin to arylpyrrole of about 1:5 to 1:20.

In practice, a synergistically effective amount of a combination of moxidectin and an arylpyrrole of formula 11 may be applied to the animal as a dip, spray, pour-on, backrubber, oiler, dustbag, powder, lotion or the like; or as an ear-tag or collar; or as an oral drench, bolus, pill, implant, capsule, feed or drinking water additive or the like; or as a parenteral injection; or by any other methods suitable for administering drugs to animals.

Advantageously, moxidectin may be formulated with an arylpyrrole of formula II, and such a formulation may then be dispersed in a solid or liquid diluent for application to the ectoparasite, its host, food supply, breeding ground or habitat, as a dilute spray or as a solid dust or dust concentrate. Customary formulation adjuvants as well as additional nontoxic pharmaceutically acceptable active ingredients may be added and are within the scope of the invention.

The active ingredients of the inventive composition may also be formulated separately as a wettable powder, emulsifiable concentrate, aqueous or liquid flowable, suspension concentrate or any one of the conventional formulations used for ectoparasite control. The separately formulated compositions may be applied sequentially to achieve a synergistic result according to the invention.

In order to present a more clear understanding of the invention, the following specific Examples are set forth below. These Examples are merely illustrative and are not to be understood as limiting the scope and underlying principles of the invention in any way. Indeed, various modifications of the invention, in addition to those illustrated and described herein, will become apparent to persons skilled in the art from the following Examples and the foregoing description. Such modifications are also intended to fall within the scope of the appended claims.

In the following Examples, synergism for two-way combinations is determined using the following formula:

$$\text{Coefficient of synergy} = z_1/Z_1 + z_2/Z_2$$

where $z_1$ and $z_2$ are the quantities of two insecticides in a mixture and $Z_1$ and $Z_2$ are the quantities of each which produce the same effect when administered separately.

A value of 1 for the coefficient of synergy indicates that the activity of the mixture is a simple additive effect of the two compounds, a value less than 1 indicates synergy, and a value greater than 1 indicates antagonism.

EXAMPLES 1–2

Evaluation of the Synergistic Ectoparasiticidal Effect of a Combination Moxidectin and an Arylpyrrole Insecticide Contact and/or ingestion activities of compounds against newly emerged larvae of the blowfly, *Lucilia sericata*, are tested using a treated paper/serum bioassay. In this assay, test compounds diluted to the required concentrations in acetone are applied to filter paper discs and allowed to dry. Bovine serum and newly emerged blowfly larvae are added to the discs and mortality assessed at 24 and 48 hours. The data obtained are shown in Table I.

As can be seen from the data in Table I application of a combination of moxidectin and the arylpyrrole chlorfenapyr gives significantly greater control than that which could be predicted from the control resulting from the application of either moxidectin or chlorfenapyr alone.

TABLE 1

| Compound | Approximate LC$_{50}$ ($\mu$g/ml) | | Coefficient of synergy | |
|---|---|---|---|---|
| | 24 hour | 48 hour | 24 hour | 48 hour |
| Example 1 | | | | |
| M* | 0.85 | 0.63 | | |
| C** | 6.54 | 4.69 | | |
| M + C(1:10) | 0.13 + 1.26 | 0.14 + 1.42 | 0.35 | 0.53 |
| Example 2 | | | | |
| M | 1.54 | 0.80 | | |
| C | 2.50 | 2.50 | | |
| M + C(1:10) | 0.14 + 1.42 | 0.125 + 1.25 | 0.65 | 0.66 |

*M = Moxidectin
**C = Chlorfenapyr

What is claimed is:

1. A method for the control of ectoparasites which comprises contacting said ectoparasites, or their host, habitat, breeding area, or food supply, with a synergistically effective amount of a combination of the macrocyclic lactone moxidectin having the formula I

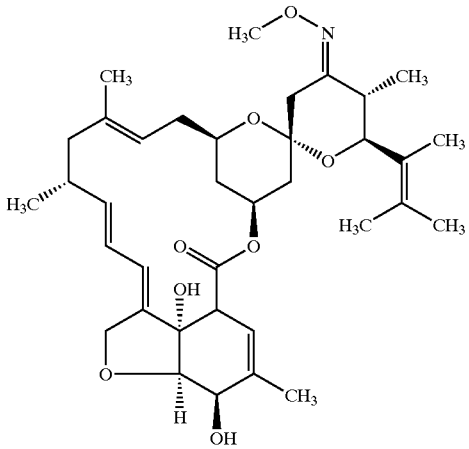

and an arylpyrrole compound of formula II

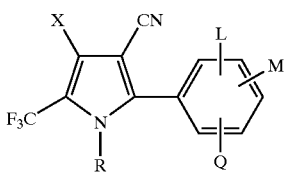

wherein R is hydrogen or $C_1$–$C_4$alkoxymethyl;
X is Cl or Br, and
L, M, and Q are each independently hydrogen, Cl, Br, I, F or $C_1$–$C_4$haloalkyl.

2. The method according to claim 1 wherein, in the arylpyrrole compound of formula II:
X is Br;
R is hydrogen or ethoxymethyl;
L and Q are hydrogen; and
M is 4-Cl or 4-Br.

3. The method according to claim 2 wherein the arylpyrrole compound is 4-bromo-2-(p-chlorophenyl)-1-(ethoxymethyl)-5-(trifluoromethyl)pyrrole-3-carbonitrile.

4. The method according to claim 2 wherein the ratio of said macrocyclic moxidectin to the arylpyrrole insecticide is about 1:5 to 1:20.

5. The method according to claim 1 wherein the ectoparasites are Diptera, Phthirapterta, Siphonaptera or Acarina.

6. The method according to claim 5 wherein the Phthiraptera is Trichodectidae, Haematopinidae or Linognathidae; the Siphonaptera is Pulicidae; the Diptera is Muscidae or Hippoboscidae; and the Acarina is Metastigmata or Mesostigmata.

7. The method according to claim 6 wherein the Muscidae is *Haematobia irritans, Musca autumnalis*, or *Stomoxys calcitrans*.

8. A method of protecting animals from infestation and attack by insects which comprises administering to the animals to be protected a synergistically effective amount of a combination of the macrocyclic lactone moxidectin having the formula I

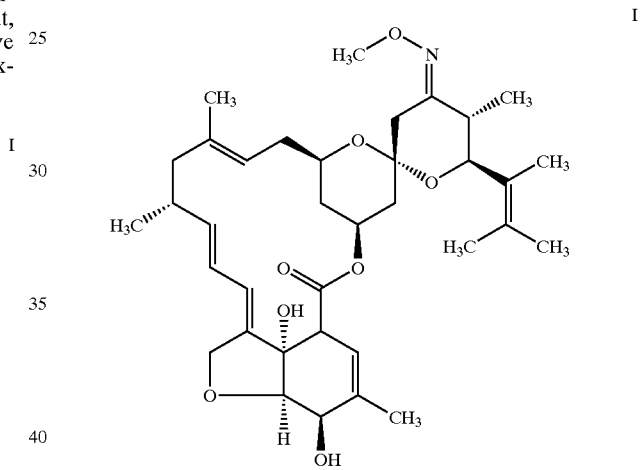

and an arylpyrrole of formula II

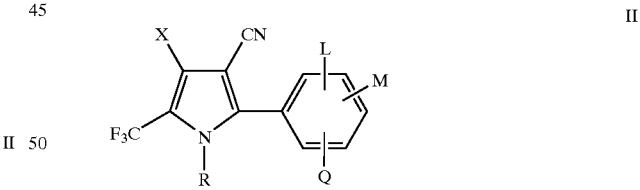

wherein R is hydrogen or $C_1$–$C_4$alkoxymethyl;
X is Cl or Br, and
L, M, and Q are each independently hydrogen, Cl, Br, I, F or $C_1$–$C_4$haloalkyl.

9. The method according to claim 8 wherein, in the arylpyrrole compound of formula II:
X is Br;
R is hydrogen or ethoxymethyl;
L and Q are hydrogen; and
M is 4-Cl or 4-Br.

10. The method according to claim 8 wherein the arylpyrrole compound is 4-bromo-2-(p-chlorophenyl)-1-(ethoxymethyl)-5-(trifluoromethyl)pyrrole-3-carbonitrile.

11. The method according to claim 10 wherein the ratio of said macrocyclic moxidectin to the arylpyrrole insecticide is about 1:5 to 1:20 and the dosage of the combination is in the approximate range of 0.01 mg/kg of body weight to 10.0 mg/kg of body weight.

12. The method according to claim 8 wherein the ratio of said macrocyclic moxidectin to the arylpyrrole insecticide is about 1:5 to 1:20.

13. The method according to claim 8 wherein the animals are cattle, sheep or buffalo.

14. The method according to claim 8 wherein the ectoparasites are is Diptera, Phthirapterta, Siphonaptera or Acarina.

15. A synergistic ectoparasiticidal composition which comprises a pharmacologically acceptable carrier and a synergistically effective amount of a combination of the macrocyclic lactone moxidectin having the formula I

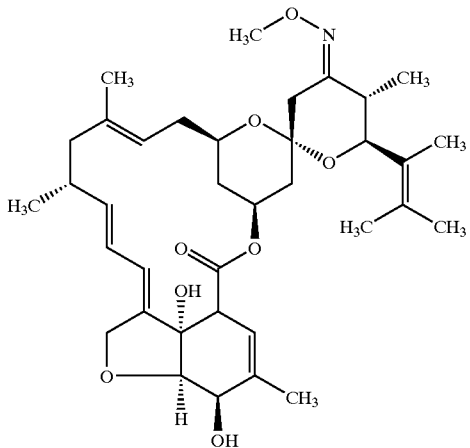

and an arylpyrrole insecticide of formula II

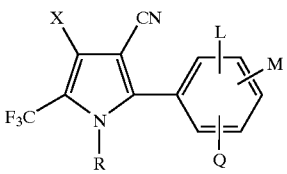

wherein R is hydrogen or $C_1$–$C_4$alkoxymethyl;

X is Cl or Br, and

L, M, and Q are each independently hydrogen, Cl, Br, I, F or $C_1$–$C_4$haloalkyl.

16. The composition according to claim 15 wherein, in the arylpyrrole compound of formula II:

X is Br;

R is hydrogen or ethoxymethyl;

L and Q are hydrogen; and

M is 4-Cl or 4-Br.

17. The composition according to claim 15 wherein the arylpyrrole compound is 4-bromo-2-(p-chlorophenyl)-1-(ethoxymethyl)-5-(trifluoromethyl)pyrrole-3-carbonitrile.

18. The composition according to claim 15 wherein the ratio of said macrocyclic endectocide moxidectin to the arylpyrrole insecticide is about 1:5 to 1:20.

19. The composition according to claim 17 wherein the ratio of said macrocyclic endectocide moxidectin to the arylpyrrole insecticide is about 1:5 to 1:20.

* * * * *